United States Patent [19]

Nishiyama et al.

[11] 4,231,787
[45] Nov. 4, 1980

[54] HERBICIDAL COMPOUND, HERBICIDAL COMPOSITION CONTAINING THE SAME, AND METHOD OF USE THEREOF

[75] Inventors: Ryuzo Nishiyama, Takatsuki; Ryohei Takahashi, Tokyo; Kanichi Fujikawa, Kyoto; Rikuo Nasu; Nobuyuki Sakashita, both of Kusatsu, all of Japan

[73] Assignee: Ishihara Sangyo Kaisha Ltd., Osaka, Japan

[21] Appl. No.: 917,758

[22] Filed: Jun. 21, 1978

Related U.S. Application Data

[62] Division of Ser. No. 734,913, Oct. 22, 1976, Pat. No. 4,105,435.

[30] Foreign Application Priority Data

Oct. 29, 1975 [JP] Japan ................................ 50-129313
Apr. 23, 1976 [JP] Japan ................................ 51-46800
Jul. 30, 1976 [JP] Japan ................................ 51-90315

[51] Int. Cl.$^2$ ............................................. A01N 9/24
[52] U.S. Cl. ........................................ 71/107; 71/122; 560/107; 568/637
[58] Field of Search ................... 71/122, 124, 107; 260/613 R, 613 B

[56] References Cited

U.S. PATENT DOCUMENTS

| | | | |
|---|---|---|---|
| 3,798,276 | 3/1974 | Bayer | 71/124 X |
| 3,966,826 | 6/1976 | Trosken | 260/613 R |
| 4,017,295 | 4/1977 | Takahashi et al. | 71/124 X |
| 4,062,896 | 12/1977 | Yoshimoto et al. | 260/613 R |

Primary Examiner—Catherine L. Mills
Attorney, Agent, or Firm—Sughrue, Rothwell, Mion, Zinn and Macpeak

[57] ABSTRACT

Phenoxypropane compounds represented by the general formula (I):

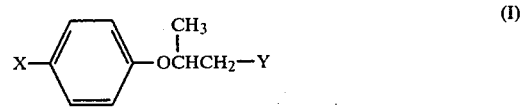

wherein X is a 4-halophenoxy group, a 2,4-dihalophenoxy group, a 4-trifluoromethylphenoxy group, a 2-halo-4-trifluoromethylphenoxy group, a 5-halopyridyl-2-oxy group or a 3,5-dihalopyridyl-2-oxy group; and Y is a halogen atom, a hydroxy group, a ($C_1$–$C_4$)-alkoxy group in which the alkyl moiety thereof may be substituted with a hydroxy group(s), a ($C_1$–$C_4$)alkylcarbonyloxy group or a phenylcarbonyloxy group in which the phenyl moiety thereof may be substituted with a halogen atoms(s), useful as a herbicide; a herbicidal composition containing the compound; and methods of controlling weeds using such materials.

1 Claim, No Drawings

HERBICIDAL COMPOUND, HERBICIDAL COMPOSITION CONTAINING THE SAME, AND METHOD OF USE THEREOF

This is a division of application Ser. No. 734,913, filed Oct. 22, 1976 now U.S. Pat. No. 4,105,435.

BACKGROUND OF THE INVENTION

1. Field of the Invention

This invention relates to a compound useful as a herbicide for agriculture and horticulture, to a herbicidal composition containing the same, and to methods of controlling weeds.

2. Description of the Prior Art

Hitherto, various herbicides have been developed and practically used for contributing to a saving of man-power and increasing the yields of agricultural products, but there is much room for improvement in such herbicides and the development of new and useful herbicides has been strongly desired. It is, of course, desirable to develop, for example, herbicides which are safe from the standpoint of environmental pollution and which have the least adverse effect on useful plants, still retaining strong herbicidal activities, but in view of the fact that the resistance of weeds to existing herbicides has increased recently, the demand for herbicides which have higher activity and are different types from existing herbicides has increased.

SUMMARY OF THE INVENTION

One object of the present invention is to provide phenoxypropane compounds which have advantageous herbicidal properties.

A further object of the present invention is to provide an effective herbicidal composition.

Still a further object of the invention is to provide a method for controlling weeds.

Accordingly, this invention, in one embodiment, provides phenoxypropane compounds represented by the general formula (I):

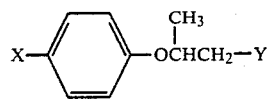

wherein X is a 4-halophenoxy group, a 2,4-dihalophenoxy group, a 4-trifluoromethylphenoxy group, a 2-halo-4-trifluoromethylphenoxy group, a 5-halopyridyl-2-oxy group or a 3,5-dihalopyridyl-2-oxy group; and Y is a halogen atom, a hydroxy group, a ($C_1$–$C_4$)alkoxy group in which the alkyl moiety thereof may be substituted with a hydroxy group(s), a ($C_1$–$C_4$)alkylcarbonyloxy group or a phenylcarbonyloxy group in which the phenyl moiety thereof may be substituted with a halogen atom(s).

In another embodiment, this invention provides a herbicidal composition comprising a herbicidally effective amount of at least one compound of the above general formula (I) and one or more agriculturally acceptable adjuvants.

In an even further embodiment of this invention, this invention provides a method of controlling weeds comprising applying a herbicidally effective amount of the above herbicidal composition to the weeds.

DETAILED DESCRIPTION OF THE INVENTION

In the definitions with respect to formula (I) representing the compound of this invention, suitable examples of halogen atoms for Y and as the halo substituent are chlorine and bromine atoms, and suitable alkyl moieties are methyl, ethyl, n-propyl, isopropyl and n-butyl groups.

The compound of this invention of the formula (I) can be prepared by one of the following methods.

(1) a method comprising reacting a lower alkyl ester, a halide or an acid anhydride of a phenoxypropionic acid represented by the formula (II)

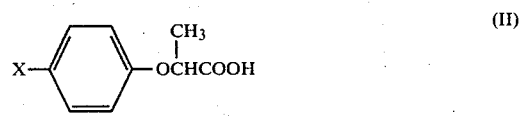

wherein X is as defined above, with an aluminum hydride compound or a boron hydride compound while refluxing in an anhydrous ether such as anhydrous diethyl ether, anhydrous tetrahydrofuran and the like for about 0.1 to about 3 hours to obtain a phenoxypropanol represented by the formula (III)

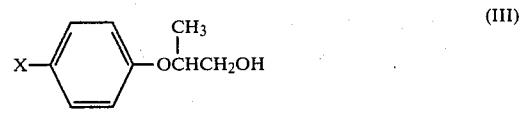

wherein X is as defined above, which corresponds to a compound of the formula (I) above wherein Y represents a hydroxy group;

(2) a method comprising halogenating a phenoxypropanol of the formula (III) above with a halogenating agent such as a hydrogen halide, a phosphorus halide, a phosphorus oxyhalide, a thionyl halide and the like at a temperature from about 0° C. to about 120° C. for about 1 to about 24 hours, advantageously in the presence of a solvent such as diethyl ether, benzene, chloroform and the like to obtain a phenoxypropyl halide represented by the formula (IV)

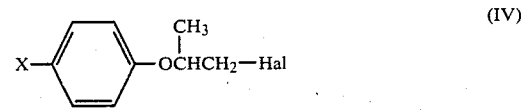

wherein X is as defined above and Hal represents a halogen atom, which corresponds to the compound of the formula (I) above wherein Y represents a halogen atom;

(3) a method comprising alkylating a phenoxypropanol of the formula (III) above with a ($C_1$–$C_4$)alkyl halide, a di($C_1$–$C_4$)-alkyl sulfate or an α-epoxide in the presence of an alkaline compound such as sodium, potassium hydroxide, sodium hydroxide and the like at a temperature from about 50° C. to about 150° C. for about 1 to about 8 hours, advantageously in the presence of a solvent such as benzene, toluene, dioxane and the like to produce an alkyl ether of a phenoxypropane represented by the formula (V)

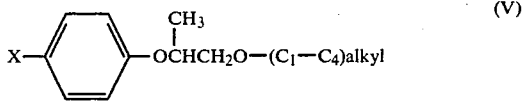

wherein X is as defined above, which corresponds to the compound of the formula (I) above wherein Y represents a ($C_1$-$C_4$)alkoxy group;

(4) a method comprising reacting a phenoxypropanol of the formula (III) above with a carboxylic acid halide represented by the formula (VI)

RCO—Hal     (VI)

wherein Hal represents a halogen atom and R represents a ($C_1$-$C_4$)alkyl group or a phenyl group which may be substituted with a halogen atom(s), advantageously in the presence of an alkaline compound such as pyridine, triethylamine, sodium carbonate, potassium carbonate and the like and a solvent such as benzene, toluene, dioxane and the like, or with a carboxylic acid anhydride represented by the formula (VII)

(RCO)$_2$O     (VII)

wherein R is as defined above, at a temperature from about 5° to about 100° C. for about 0.5 to about 3 hours, advantageously in the presence of a solvent such as benzene, toluene, dioxane and the like, to produce a compound represented by the formula (VIII)

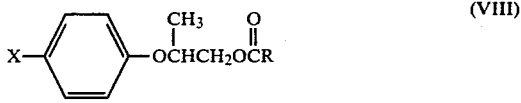

wherein X and R are as defined above, which corresponds to the compound of the formula (I) above wherein Y represents a ($C_1$-$C_4$)-alkylcarbonyloxy group or a phenylcarbonyloxy group.

The following Preparation Examples are given to illustrate the preparation of some typical compounds of this invention, but they are not to be construed as limiting the present invention. Unless otherwise indicated, all parts, percents, ratios and the like are by weight.

PREPARATION EXAMPLE 1

Preparation of β-[4-(4-Trifluoromethylphenoxy)phenoxy]propanol 6.6 g of methyl-α-[4-(4-trifluoromethylphenoxy)phenoxy]propionate was dissolved in 15 ml of anhydrous diethyl ether, and the solution was added slowly to a dispersion of 0.4 g of lithium aluminum hydride in 50 ml of anhydrous diethyl ether while cooling. After completion of the addition, the mixture was refluxed at about 35° C. for 10 minutes to complete the reaction. The reaction mixture was poured into an appropriate amount of ice water to decompose any remaining unreacted lithium aluminum hydride, and 10% sulfuric acid was added to the mixture. The ethereal layer was separated, extracted twice with diethyl ether and dried over anhydrous sodium sulfate. The ether was removed from the dried extract and the resulting residue was distilled under reduced pressure to obtain 4.8 g of the desired product having a boiling point of 165° to 168° C./3 mmHg.

PREPARATION EXAMPLE 2

Preparation of β-[4-(4-Trifluoromethylphenoxy)phenoxy]propylbenzoate 1 g of β-[4-(4-Trifluoromethylphenoxy)phenoxy]propanol and 0.25 g of pyridine were dissolved in 10 ml of benzene, and 0.45 g of benzoyl chloride was added slowly to the solution while cooling. After completion of the addition, the mixture was allowed to react at a temperature of 20° C. for 1 hour, and the reaction mixture was poured into an appropriate amount of water. The benzene layer was separated and, after drying, benzene was removed to obtain 1 g of the desired product ($n_D^{20}$ 1.541) as an oily substance.

PREPARATION EXAMPLE 3

Preparation of β-[4-(3,5-Dichloropyridyl-2-oxy)phenoxy]propanol 6.8 g methyl-α-[4-(3,5-dichloropyridyl-2-oxy)phenoxy]-propionate was dissolved in 50 ml of anhydrous tetrahydrofuran and the solution was added slowly to a dispersion of 0.4 g of lithium aluminum hydride in 50 ml of anhydrous tetrahydrofuran while cooling. After completion of the addition, the mixture was refluxed at about 35° C. for 20 minutes to complete the reaction. The reaction mixture was poured into an appropriate amount of ice water to decompose any remaining unreacted lithium aluminum hydride, and 10% sulfuric acid was added to the mixture. The organic layer was separated, extracted twice with diethyl ether and dried over anhydrous sodium sulfate. The solvent was removed from the dried extract and the resulting residue was distilled under reduced pressure to obtain 4.2 g of the desired product having a boiling point of 179° to 182° C./1.5 mmHg.

PREPARATION EXAMPLE 4

Preparation of α-Methoxy-β-[4-(4-trifluoromethylphenoxy)-phenoxy]-propane 6 g of β-[4-(4-trifluoromethylphenoxy)phenoxy]-propanol was dissolved in 30 ml of dioxane and 0.46 g of sodium was added to the solution. The mixture was then heated for 3 hours while refluxing. 3.1 g of methyl iodide was added thereto and the resulting mixture was heated for 6 hours while refluxing. The reaction mixture was then poured into an appropriate amount of water and extracted with diethyl ether. The extract was washed with water and dried over anhydrous sodium sulfate. The ether was removed by distillation and the residue was distilled under reduced pressure to obtain 4.2 g of the desired product having a boiling point of 160° to 165° C./2 mmHg.

PREPARATION EXAMPLE 5

Preparation of β-[4-(3,5-Dichloropyridyl-2-oxy)phenoxy]propyl Chloride 3.6 g of β-[4-(3,5-dichloropyridyl-2-oxy)phenoxy]-propanol and 1.1 g of pyridine were dissolved in 50 ml of anhydrous diethyl ether, and 1.5 g of thionyl chloride was added dropwise to the solution while cooling. The mixture was then heated for 1 hour while refluxing with stirring. The reaction mixture was poured into an appropriate amount of water and the mixture was extracted with diethyl ether. The extract was washed with water and dried over anhydrous sodium sulfate. The ether was removed from the dried extract by distillation, and the residue was distilled under reduced pressure to obtain 2.9 g of the desired product having a boiling point of 180° to 186° C./1.5 mmHg.

PREPARATION EXAMPLE 6

Preparation of α-(2′-Hydroxy)propoxy-β-[4-(4-trifluoromethylphenoxy)phenoxy]propane To 0.4 ml of an aqueous solution containing 8 g of β-[4-(4-trifluoromethylphenoxy)phenoxy]propanol and 0.2 g of potassium hydroxide was added 1.6 g of propylene oxide, and the mixture was heated for 3 hours while refluxing with stirring. The reaction mixture was extracted with chloroform, and the extract was washed with water and dried over anhydrous sodium sulfate. Chloroform was then removed by distillation from the extract and the residue was distilled under reduced pressure to obtain 6.5 g of the desired product having a boiling point of 185° to 192° C./2 mmHg.

PREPARATION EXAMPLE 7

Preparation of β-[4-(2,4-Dichlorophenoxy)phenoxy]propanol 48 g of ethyl-α-[4-(2,4-dichlorophenoxy)phenoxy]-propionate was dissolved in 80 ml of anhydrous diethyl ether and the solution was added dropwise to a dispersion of 5 g of lithium aluminum hydride in 200 ml of anhydrous diethyl ether while cooling. After completion of the addition, the mixture was allowed to stand for 12 hours at room temperature and then heated under refluxing for 1.5 hours to complete the reaction. The reaction mixture was poured into an appropriate amount of ice water, and the ethereal layer was separated. The ethereal layer was again extracted with diethyl ether and the extract was dried over anhydrous sodium sulfate. The ether was removed by distillation from the dried extract, and the residue was distilled under reduced pressure to obtain 40 g of the desired product having a boiling point of 201° to 205° C./2 mmHg.

PREPARATION EXAMPLE 8

Preparation of α-Methoxy-β-[4-(2,4-dichlorophenoxy)phenoxy]propane 6 g of β-[4-(2,4-dichlorophenoxy)phenoxy]propanol was dissolved in 3.4 g of 30% aqueous sodium hydroxide. The solution was heated at a temperature of 60° C., then 3.1 g of dimethyl sulfate was added dropwise to the solution with stirring and the mixture was allowed to react for 1.5 hours. The reaction mixture was poured into an appropriate amount of water, and the mixture was extracted with diethyl ether. The extract was washed with water and dried over anhydrous sodium sulfate, and the ether was removed by distillation. The residue was distilled under reduced pressure to obtain 3.0 g of the desired product having a boiling point of 182° to 185° C./1.5 mmHg.

PREPARATION EXAMPLE 9

Preparation of β-[4-(2,4-Dichlorophenoxy)phenoxy]propyl Chloride 3.0 g of β-[4-(2,4-Dichlorophenoxy)phenoxy]-propanol and 1.1 g of pyridine were dissolved in 50 ml of anhydrous diethyl ether, and 1.5 g of thionyl chloride was added dropwise to the solution while cooling. The mixture was then heated for 1 hour while refluxing. The reaction mixture was poured into an appropriate amount of water, and the mixture was extracted with diethyl ether. The extract was washed with water and dried over anhydrous sodium sulfate. The ether was removed by distillation and the residue was distilled under reduced pressure to obtain 2.5 g of the desired product having a boiling point of 192° to 194° C./2 mmHg.

Typical compounds prepared by the above processes are listed below. Reference by compound number designation set forth below will be made hereinafter in the specification.

Compound No. 1
β-[4-(4-trifluoromethylphenoxy)phenoxy]propanol bp 165°–168° C./3 mmHg Compound No. 2
β-[4-(4-trifluoromethylphenoxy)phenoxy]propyl benzoate $n_D^{20}$ 1.541

Compound No. 3
β-[4-(4-chlorophenoxy)phenoxy]propanol bp 173°–176° C./2 mmHg

Compound No. 4
β-[4-(3,5-dichloropyridyl-2-oxy)phenoxy]propanol bp 179°–182° C./1.5 mmHg Compound No. 5
β-[4-(5-bromopyridyl-2-oxy)phenoxy]propanol bp 204°–208° C./2 mmHg Compound No. 6
β-[4-(3,5-dibromopyridyl-2-oxy)phenoxy]propanol bp 214°–219° C./1.5 mmHg Compound No. 7
β-[4-(4-bromophenoxy)phenoxy]propyl-p-chlorobenzoate Compound No. 8
β-[4-(5-chloropyridyl-2-oxy)phenoxy]propyl acetate Compound No. 9
β-[4-(3,5-dibromopyridyl-2-oxy)phenoxy]-propanol Compound No. 10
β-[4-(4-trifluoromethylphenoxy)phenoxy]propyl chloride bp 138°–142° C./2 mmHg Compound No. 11
β-[4-(3,5-dichloropyridyl-2-oxy)phenoxy]propyl chloride bp 180°–186° C./1.5 mmHg Compound No. 12
β-[4-(4-trifluoromethylphenoxy)phenoxy]propyl bromide bp 155°–160° C./2 mmHg Compound No. 13
β-[4-(3,5-dichloropyridyl-2-oxy)phenoxy]propyl bromide bp 190°–195° C./1 mmHg Compound No. 14
α-methoxy-β-[4-(4-trifluoromethylphenoxy)phenoxy]-propane bp 160°–165° C./1 mmHg Compound No. 15
α-(2′-hydroxy)propoxy-β-[4-(4-trifluoromethylphenoxy)-phenoxy]propane bp 185°–192° C./2 mmHg Compound No. 16
β-[4-(2-chloro-4-trifluoromethylphenoxy)phenoxy]-propyl chloride bp 141°–145° C./2 mmHg Compound No. 17
α-ethoxy-β-[4-(2-chloro-4-trifluoromethylphenoxy)-phenoxy]propane bp 172°–175° C./2.5 mmHg Compound No. 18
α-methoxy-β-[4-(5-chloropyridyl-2-oxy)phenoxy]-propane bp 164°–168° C./2 mmHg Compound No. 19
  α-ethoxy-β-[4-(3,5-dichloropyridyl-2-oxy)phenoxy]-propane bp 179°–184° C./1.5 mmHg
Compound No. 20
  α-n-propoxy-β-[4-(3,5-dichloropyridyl-2-oxy)-phenoxy]-propane bp 182°–185° C./1.5 mmHg
Compound No. 21
  α-(2'-hydroxy)propoxy-β-[4-(5-chloropyridyl-2-oxy)-phenoxy]propane
Compound No. 22
  β-[4-(2,4-dichlorophenoxy)phenoxy]propanol bp 201°–205° C./2 mmHg
Compound No. 23
  α-methoxy-β-[4-(2,4-dichlorophenoxy)phenoxy]-propane bp 182°–185° C./1.5 mmHg
Compound No. 24
  β-[4-(2,4-dichlorophenoxy)phenoxy]propyl chloride bp 192°–194° C./2 mmHg
Compound No. 25
  β-[4-(2,4-dichlorophenoxy)phenoxy]propyl bromide
Compound No. 26
  α-ethoxy-β-[4-(2,4-dichlorophenoxy)phenoxy]-propane
Compound No. 27
  α-n-propoxy-β-[4-(2,4-dichlorophenoxy)phenoxy]-propane
Compound No. 28
  α-isopropoxy-β-[4-(2,4-dichlorophenoxy)phenoxy]-propane
Compound No. 29
  α-n-butoxy-β-[4-(2,4-dichlorophenoxy)phenoxy]-propane Herbicidal compositions containing the phenoxypropane compounds of the present invention having the formula (I) above as active ingredients exhibit excellent herbicidal activities as shown in the Test Examples hereinafter described. In particular, it is noted that these phenoxypropane compounds exhibit a peculiar selective herbicidal activity on gramineous weeds without causing any phytotoxic activity on broad leaved weeds. Thus, by taking advantage of such selective herbicidal activities of the phenoxypropane compounds, the herbicidal compositions of this invention make it possible to control only noxious gramineous weeds which grow in crops cultivated on upland farms by applying the compositions in various application manners. Of course, the herbicidal compositions of the present invention can also be applied broadly to orchards, forests, various non-agricultural lands, paddy fields (low land fields) in addition to the upland farms by suitably selecting the application procedure, the amount of the composition to be used, etc. Also, such herbicidal compositions can be applied using various techniques such as soil treatment, foliar treatment and the like in a similar manner to conventional herbicidal compositions, as is well known in the art. A particularly preferred procedure for using the herbicidal compositions of this invention for crops cultivated on upland farms is soil treatment.

A suitable rate of application varies according to various factors such as the climatic conditions, the soil conditions, the form of the chemical, the time of application, the method of application, or the types of cultivated crops to which it is applied and the main weeds to be controlled. When the compound of this invention is used in the form of a solid preparation (e.g., dust or granules), the amount of the active ingredient is 0.1 to 1,000 g per are (100 m$^2$), preferably 1 to 500 g, and more preferably 5 to 100 g, per are.

The compound of this invention can be dispersed in water to produce an aqueous dispersion.

The compound of this invention can also be formulated into various forms such as an emulsifiable concentrate, a wettable powder, a water-miscible solution, a dust or granules by optionally incorporating conventional agriculturally acceptable adjuvants, for example, a carrier such as diatomaceous earth, calcium hydroxide, calcium carbonate, talc, white carbon, kaolin, bentonite, or Jeeklite (trade name for a zeolite, produced by Jeeklite Co.), solvents such as n-hexane, toluene, xylene, solvent naphtha, ethanol, dioxane, acetone, isophorone, methyl isobutyl ketone, dimethylformamide, dimethyl sulfoxide or water, or an anionic or nonionic surface active agent such as a sodium alkylsulfate, a sodium alkylbenzenesulfonate, sodium ligninsulfonate, a polyoxyethylene lauryl ether, a polyoxyethylene alkylaryl ether, a polyoxyethylene fatty acid ester, or a polyoxyethylene sorbitan fatty acid ester. A suitable ratio of the compound of this invention to the adjuvant(s) ranges from about 1 to 90:99 to 10 by weight, preferably 1 to 70:99 to 30 by weight.

The herbicidal composition of this invention can also be mixed or used together with suitable agricultural chemicals such as other herbicides, insecticides or fungicides, or mixed with an agricultural agent such as a fertilizer or soil conditioner or soil or sand, at the time of formulation or application. Sometimes, such joint usage brings about improved effects.

Typical examples of herbicidal formulations containing a compound of this invention are shown below.

FORMULATION EXAMPLE 1

| | | |
|---|---|---|
| (1) | β-[4-(3,5-Dichloropyridyl-2-oxy)phenoxy]-propanol | 20 wt.parts |
| (2) | Xylene | 60 wt.parts |
| (3) | Sorpol 2806B (trade name for a mixture of a polyoxyethylene phenyl phenol derivative, a polyoxyethylene alkylaryl ether, a polyoxyethylene sorbitan alkylate and an alkylaryl sulfonate produced by Toho Chemical Co., Ltd.) | 20 wt.parts |

The components (1) to (3) were uniformly mixed to form an emulsifiable concentrate.

FORMULATION EXAMPLE 2

| | | |
|---|---|---|
| (1) | Jeeklite | 78 wt.parts |
| (2) | Lavelin S (trade name for a sodium naphthalene sulfonate-formaldehyde condensate produced by Daiichi Kogyo Seiyaku Co., Ltd.) | 2 wt.parts |
| (3) | Sorpol 5039 (trade name for a sulfate of polyoxyethylene alkylaryl ether produced by Toho Chemical Co., Ltd.) | 5 wt.parts |
| (4) | Carplex (trade name for a white carbon produced by Shionogi Seiyaku Co., Ltd.) | 15 wt.parts |

Components (1) to (4) were mixed and the mixture obtained was then mixed with β-[4-(4-trifluoromethylphenoxy)phenoxy]propanol in a ratio of 4:1 by weight to form a wettable powder.

FORMULATION EXAMPLE 3

(1) α-Methoxy-β-[4-(4-trifluoromethylphenoxy)-

-continued

| | |
|---|---|
| phenoxy]propane | 20 wt.parts |
| (2) Xylene | 60 wt.parts |
| (3) Sorpol 2806B | 20 wt.parts |

Components (1) to (3) were uniformly mixed to form an emulsifiable concentrate.

FORMULATION EXAMPLE 4

| | |
|---|---|
| (1) Bentonite | 58 wt.parts |
| (2) Jeeklite | 30 wt.parts |
| (3) Sodium ligninsulfonate | 5 wt.parts |

Components (1) to (3) were mixed and granulated. A solution prepared by diluting 7 wt.parts of $\beta$-[4-(3,5-dichloropyridyl-2-oxy)phenoxy]propyl chloride with acetone was sprayed on the granulated components to form granules.

FORMULATION EXAMPLE 5

| | |
|---|---|
| (1) $\alpha$-Methoxy-$\beta$-[4-(2,4-dichlorophenoxy)-phenoxy]propane | 20 wt.parts |
| (2) Xylene | 60 wt.parts |
| (3) Sorpol 2806B | 20 wt.parts |

Components (1) to (3) were uniformly mixed to form an emulsifiable concentrate.

FORMULATION EXAMPLE 6

| | |
|---|---|
| (1) Bentonite | 58 wt.parts |
| (2) Jeeklite | 30 wt.parts |
| (3) Sodium ligninsulfonate | 5 wt.parts |

Components (1) to (3) were mixed and granulated. A solution prepared by diluting 7 wt.parts of $\beta$-[4-(2,4-dichlorophenoxy)phenoxy]propyl chloride with acetone was sprayed on the granulated components to form granules.

The herbicidal activity of the compound of this invention was tested as shown below and the results obtained are also shown below.

TEST EXAMPLE 1

Each 1/3,000 are (1/30 m²) flat was charged with soil to provide upland farm conditions. Predetermined amounts of seeds of edible barnyard grass, radish and soybeans were sown and covered with soil containing seeds of large crab-grass (*Digitaria adscendens* HENR.), green foxtail (*Setaria viridis* BEAUV.) and barnyard grass (*Echinochloa crus-galli* BEAUV.) as gramineous weeds to a thickness of about 1 cm. Three days after sowing, an aqueous dispersion of each of the compounds shown in Table 1 was sprayed thereon, and the growth of the weeds was visually evaluated 20 days after the spraying. The results obtained are shown in Table 1. The degree of growth inhibition shown in Table 1 was evaluated on a scale of 10 grades in which 10 indicates that growth was completely inhibited and 1 indicates no inhibition.

TABLE 1

| Compound No. | Amount of Active Ingredient (g/are) | Degree of Growth Inhibition | | | |
|---|---|---|---|---|---|
| | | Edible Barnyard Grass | Rad-ish | Soy-beans | Gramineous Weeds |
| 1 | 100 | 10 | 1 | 1 | 10 |
| | 50 | 10 | 1 | 1 | 10 |
| 2 | 100 | 10 | 1 | 1 | 10 |
| | 50 | 10 | 1 | 1 | 10 |
| 3 | 100 | 10 | 1 | 1 | 10 |
| | 50 | 10 | 1 | 1 | 10 |
| 4 | 100 | 10 | 1 | 1 | 10 |
| | 50 | 10 | 1 | 1 | 10 |
| 5 | 100 | 10 | 1 | 1 | 10 |
| | 50 | 10 | 1 | 1 | 10 |
| 6 | 100 | 10 | 1 | 1 | 10 |
| | 50 | 10 | 1 | 1 | 10 |
| 8 | 100 | 9 | 1 | 1 | 10 |
| | 50 | 8 | 1 | 1 | 10 |
| 10 | 100 | 10 | 1 | 1 | 10 |
| | 50 | 10 | 1 | 1 | 10 |
| 11 | 100 | 10 | 1 | 1 | 10 |
| | 50 | 10 | 1 | 1 | 10 |
| 12 | 100 | 10 | 1 | 1 | 10 |
| | 50 | 10 | 1 | 1 | 10 |
| 13 | 100 | 10 | 1 | 1 | 10 |
| | 50 | 10 | 1 | 1 | 10 |
| 14 | 100 | 10 | 1 | 1 | 10 |
| | 50 | 10 | 1 | 1 | 10 |
| 15 | 100 | 10 | 1 | 1 | 10 |
| | 50 | 10 | 1 | 1 | 10 |
| 16 | 100 | 10 | 1 | 1 | 10 |
| | 50 | 10 | 1 | 1 | 10 |
| 17 | 100 | 10 | 1 | 1 | 10 |
| | 50 | 10 | 1 | 1 | 10 |
| 18 | 100 | 10 | 1 | 1 | 10 |
| | 50 | 9 | 1 | 1 | 10 |
| 19 | 100 | 10 | 1 | 1 | 10 |
| | 50 | 10 | 1 | 1 | 10 |
| 20 | 100 | 10 | 1 | 1 | 10 |
| | 50 | 10 | 1 | 1 | 10 |
| 21 | 100 | 10 | 1 | 1 | 10 |
| | 50 | 10 | 1 | 1 | 10 |
| 22 | 100 | 10 | 1 | 1 | 10 |
| | 50 | 9 | 1 | 1 | 10 |
| 23 | 100 | 10 | 1 | 1 | 10 |
| | 50 | 7 | 1 | 1 | 10 |
| 24 | 100 | 10 | 1 | 1 | 10 |
| | 50 | 10 | 1 | 1 | 10 |

TEST EXAMPLE 2

Each 1/10,000 are (1/100 m²) pot was charged with soil and completely saturated with water. A predetermined amount of air-dried seeds of barnyard grass was sown and lightly covered with soil. When the barnyard grass germinated above the ground, water was put into the pot to a depth of 3 cm to provide flooded conditions, and an aqueous dispersion of each of the compounds shown in Table 2 was poured into the pot. Twenty days after treatment with the dispersion, the surviving barnyard grass in the pot was pulled out, dried in air, and weighed. The percentage of the amount of surviving weeds based on the untreated pot was calculated, and the degree of growth determined (with 0% meaning no growth and 100% no inhibition). The results obtained are shown in Table 2.

TABLE 2

| | Degree of Growth (%) | |
|---|---|---|
| | Amount of Active Ingredient (g/are) | |
| Compound No. | 5 | 2.5 |
| 1 | 0 | 0 |
| 2 | 0 | 0 |
| 3 | 0 | 0 |

TABLE 2-continued

| | Degree of Growth (%) | |
|---|---|---|
| | Amount of Active Ingredient (g/are) | |
| Compound No. | 5 | 2.5 |
| 4 | 0 | 0 |

While the invention has been described in detail and with reference to specific embodiments thereof, it will be apparent to one skilled in the art that various changes and modifications can be made therein without departing from the spirit and scope thereof.

What is claimed is:

1. A method for controlling noxious gramineous weeds in the presence of cultivated broad leaf crops which comprises applying a herbicidally effective amount of a herbicidal composition which consists essentially of a herbicidally effective amount of at least one compound having the formula (I):

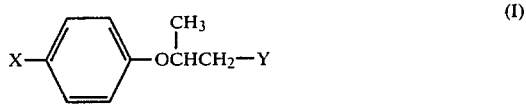

wherein X is 4-trifluoromethylphenoxy group; and Y is a hydroxy group or a phenylcarbonyloxy group as an active ingredient and an agriculturally acceptable adjuvant.

* * * * *